Figure 1:
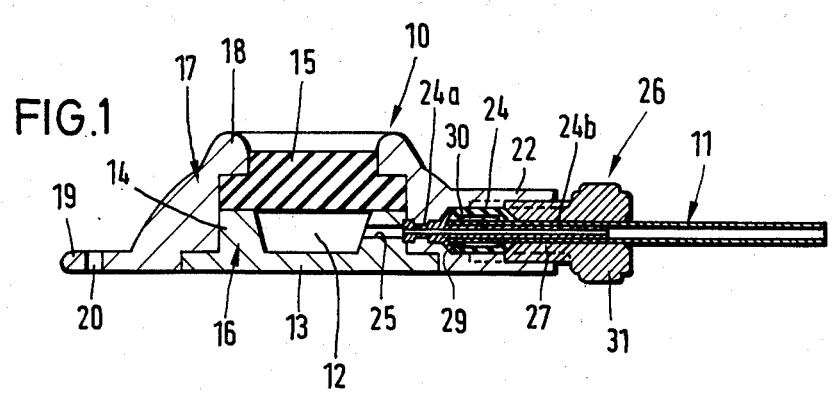

United States Patent [19]

Stöber et al.

[11] Patent Number: 4,704,103
[45] Date of Patent: Nov. 3, 1987

[54] IMPLANTABLE CATHETER MEANS

[75] Inventors: Herbert Stöber, Staufenberg; Norbert Brencher, Hess. Lichtenau, both of Fed. Rep. of Germany

[73] Assignee: Burron Medical Inc., Bethlehem, Pa.

[21] Appl. No.: 898,502

[22] Filed: Aug. 21, 1986

[51] Int. Cl.⁴ .................. A61M 25/00; A61M 5/00
[52] U.S. Cl. ................................................ 604/175
[58] Field of Search ............ 604/93, 175, 241–243, 604/283; 285/341

[56] References Cited

U.S. PATENT DOCUMENTS

| | | | |
|---|---|---|---|
| 2,855,927 | 10/1958 | Henderson | 604/243 X |
| 3,472,532 | 10/1969 | Leopold et al. | 285/341 X |
| 3,738,688 | 6/1973 | Racine | 285/341 X |
| 4,187,848 | 2/1980 | Taylor | 604/243 |
| 4,323,065 | 4/1982 | Kling | 604/283 |
| 4,529,230 | 7/1985 | Fatula | 285/341 |
| 4,543,088 | 9/1985 | Bootman et al. | 604/93 |
| 4,569,675 | 2/1986 | Prosl et al. | 604/175 |

FOREIGN PATENT DOCUMENTS 0134745  3/1985  European Pat. Off. ............ 604/175

Primary Examiner—Dalton L. Truluck
Attorney, Agent, or Firm—Shoemaker and Mattare, Ltd.

[57] ABSTRACT

The implantable catheter means comprises a capsula (10) having a pierceable top wall (15). A catheter (11) extending into a cavity (12) of said capsula (10) is fixed thereto by an elastomeric clamping member (30) arranged inside a connecting piece (22) which has an internal thread (23) engaged by an external thread of a pressure member (26). By turning the pressure member (26), the clamping member (30) is deformed to press against the periphery of the catheter to fix it and to seal it relative to the capsula (10). The lateral dimensions of the capsula (10) are not increased by the connecting piece (22). The catheter coupling may be easily tightened and released, and it safely prevents the catheter from being extracted.

9 Claims, 3 Drawing Figures

IMPLANTABLE CATHETER MEANS

The invention relates to an implantable catheter means, in particular for a long-term therapy with cytostatic compositions.

Certain therapies require a constant administration of pharmaceuticals into the blood system of a patient. It has been known to implant subcutaneously in a patient a capsula which is connected to a catheter hose whose other end extends into a vessel. To administer a medicament, a hollow needle is introduced through the patient's skin into the capsula which, to this effect, comprises a membrane-type upper wall adapted to be pierced by the hollow needle. Through the latter, the medicament may be injected by a syringe into the capsula.

In a known implantable catheter means (German Patent No. 33 09 788), the capsula comprises a radially projecting flange elongating the bottom wall. Above the flange, a connecting piece projecting from the peripheral wall of the capsula extends far beyond the flange. The end of the catheter is provided with a flexible hose portion that may be slipped over the connecting piece to connect the catheter to the capsula. It is not favorable that the catheter has a predetermined length which may not be reduced by the user because, otherwise, the hose portion slipped on the connecting piece would be cut off as well. Considerable force is required to couple the catheter to the capsula to ensure a safe seat. On the other hand, the coupling of the catheter to the connecting piece is not safe because, in case of an improper handling, the catheter may slip off the connecting piece. After all, it is disadvantageous that the connecting piece projects far beyond the capsula contour thus probably causing problems when the capsula is applied.

In another known implantable catheter means (German Utility Model No. 84 34 177), the capsula also includes a laterally protruding bottom flange and a connecting piece laterally protruding past the bottom flange. the catheter end may be introduced through the connecting piece into the capusla cavity, the fixation of the catheter to the connecting piece being performed by a pressure member adapted to slide on the catheter and to be fixed to the connecting piece by a snap fastener. Inside the pressure member, there is an elastomeric clamping piece which is axially pressed by the end of the connecting piece inside the pressure member and which is deformed radially thus tightening the catheter and sealing the catheter passageway. It is unfavorable again that the connecting piece must be extremely long and that its total size has to be available to slip thereover the pressure member. Further, much force is required to detach the catheter from the capsula, whereby the pressure member even may be destroyed.

It is the object of the invention to provide an implantable catheter means permitting to safely and quickly couple the catheter to the connecting piece, and adapted, upon demand, to be easily detachable as well as requiring little space so that the dimensions of the capsula are not increased substantially by the connecting piece.

The problem is solved by the features of the invention.

In the implantable catheter means of the invention, the conencting piece of the capsula is provided with an internal thread into which an external thread of the pressure member may be screwed. The outer contour or the peripheral face of the connecting piece not being required to establish the connection with the catheter, the peripheral face of the connecting piece need not be round but may be integrally formed to the flange without laterally projecting beyond it (i.e. in longitudinal direction of the radial connecting member). With respect to the connecting piece, the catheter is exclusively fixed and sealed internally, in that the pressure member is screwed into the inner thread of the connecting piece in axially deforming the clamping member. Thus, no other elements are slipped over the connecting piece and no elements are fixed externally on its periphery so that the radial extent of the capsula is small.

The catheter which does not comprise a specifically formed connecting member may be cut by the user to an optional length. The catheter end need be only slipped through the connecting piece into the cavity of the capsula, the catheter being fixed by radially pressing the clamping member against the catheter.

The elastomeric clamping member is preferably deformed by two end faces designed as an internal cone and of which one is provided at the capsula and the other at the pressure member. Within the ranges of the conical end faces, the radial pressing of the clamping member to the catheter is intensified thus producing two consecutively arranged sealing faces at the two ends of the clamping member.

Furthermore, the invention permits to provide a compact capsula easily producible which consists of two housing portions put into one another and fixing the perforated top wall or membrane.

The invention also relates to a catheter means in which one end of a catheter is detachably connectible to a connection unit, e.g. a capsula or syringe.

According to the invention, a support canula is provided in the catheter section on which the clamping piece is seated that is axially compressed for fixing the catheter. The support canula which consists of a thin-walled rigid tube, preferably of metal, supports the catheter from the inside and inhibits a constriction of the catheter lumen by the radially inwardly pressing clamping member.

The support canula integrally joined to the connection unit projects coaxially into or through the connecting piece. The outer diameter of the support canula corresponds to the internal diameter of the catheter thus allowing to easily slip the catheter end section over the support canula.

Figure 2:
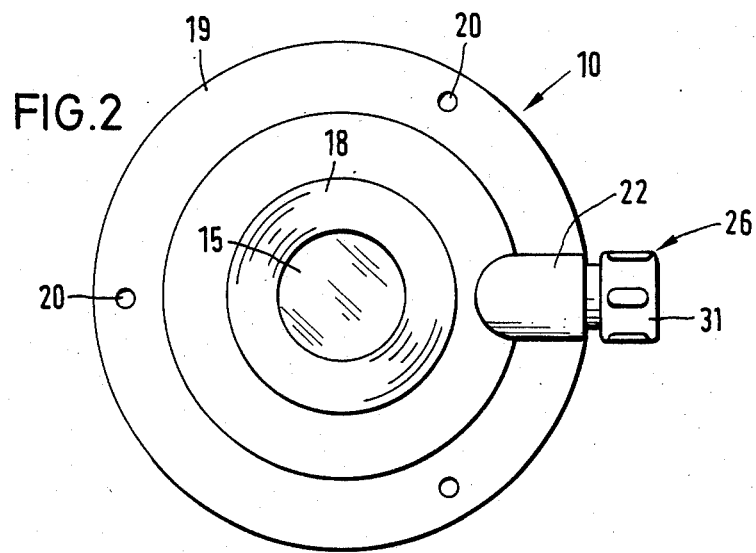
Figure 3:
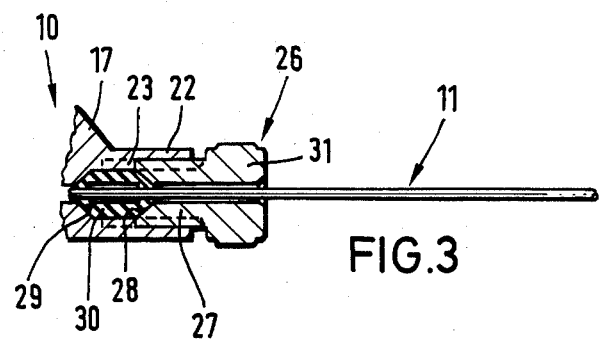

Embodiments of the invention will be explained hereunder in more detail with reference to the drawings in which FIG. 1 is a longitudinal section of the capsula having the catheter end inserted, in a first embodiment, FIG. 2 is a plan view of the capsula according to FIG. 1, FIG. 3 is a longitudinal section of the connecting piece with the catheter tightened, in a second embodiment.

The catheter means comprises a capsula 10 and a catheter in the form of a flexible hose the end of which is inserted in a cavity 12 in the interior of capsula 10. The cavity 12 is provided to receive a liquid medicament introducible through the catheter 11 into a blood vessel of a patient. The capsula 10 comprises a bottom wall 13, a peripheral wall 14 and a pierceable top wall 15, said walls 13, 14 and 15 enclosing the cavity 12. The top wall 15 is formed by a membrane which may be pierced by a (non-illustrated) hollow needle and which is sealingly closed again upon the extraction of the hollow neddle.

The housing of capsula 10 consists of two portions 16 and 17, the inner portion 16 forming the bottom wall 13 and the lower part of the peripheral wall 14, while the outer housing portion 17 peripheral wall 14, while the inner housing portion 16 projects beyond it upwardly. The upper end of housing portion 17 includes an annular bead-shaped collar 18 which presses from the top against the border of the upper wall 15 to keep said edge pressed against the upper end side of the inner housing portion 16. The housing portions 16 and 17 are connected by bonding or welding. The bead-shaped collar 18 forms a funnel-type limitation of the top wall 15, thus making it easier to find the top wall and to perform the penetration by the hollow needle.

The capsula 10 is implanted subcutaneously, top wall 15 being confronted with the patient's skin, and being directed outwardly accordingly. The border of the top wall 15 is stepped so that the upper part of the top wall extends into and upwardly from the region enclosed by collar 18.

Seen in plan view, the outer housing portion 17 is circular. Its lower end is provided with a radially projecting annular flange 19 containing holes 20 for the fixation of the capsula to the face. Flange 19 encompassing the bottom wall 13 of the cavity 12 is in one and the same plane with the bottom wall. The housing portions 16 and 17 are fitted into one another such as to exclude any play (without cavities) and to obtain a continuous plane underside of the capsula 10.

The connecting member 22 is integrally formed in one piece to the outer housing portion 17 and extends upwardly from the flange 19 to pass over into the lateral wall region of the outer housing portion 17. As particularly obvious from FIG. 2, the connecting piece 22 does not project laterally beyond flange 19 thus not increasing the radial dimensions of the capsula.

The connecting piece 22 contains a cylindrical clamping space whose peripheral wall, on part of its length, is formed by the internal thread 23. Catheter 11 extends into the connecting piece 22, while the support canula 24 extends into the catheter end to be fixed, the support canula containing a section 24a fixed to the capsula 10, e.g. enclosed by injecting therearound the plastic material of the housing portion, and a straight tubular support section 24b which coaxially extends in the connecting piece 22 to project unsupportedly to the outside. The support canula 24 accomodates a longitudinal passageway extending from one end to the other and communicating with the cavity 12 through a bore 25 of housing portion 16. The pressure member 26 is slipped on the catheter 11 and includes a longitudinal passageway in which the catheter 11 is easily displaceable. The pressure member 26 is provided with a thread shaft 27 whose outer thread is in engagement with the internal thread 23. The rear end of the thread shaft 27 is provided with a turning knob 31 which, by means of its gripping ribs may be rotated. The support section 24b of the support canula 24 extends in the catheter 11 as fas as to the pressure member 26.

The front end wall of the thread shaft 27 of the pressure member 26 is provided with a funnel-shaped recess 28 limiting the clamping space. The opposite limitation of the latter is formed by the funnel-shaped end wall 29 of the support flange of the support canula 24. The catheter end abuts against end wall 29.

The clamping space is substantially filled by the elastomeric clamping member 30 which, according to FIG. 1, is relaxed. The clamping member consists of a tubular ring of elastomeric material. The catheter 11 traverses the central aperture of the ring, and the end walls of the ring are shaped frustoconically in adaptation to the funnel-shaped end walls 28 and 29.

If the pressure member 26 is screwed into the internal thread 23, the clamping member 30 (relative to catheter 11), is axially compressed whereby, at the same time, it is flared radially, the maximum radial pressure being performed in the range of the funnel-shaped end walls 28 and 29 (FIG. 3), so that the two ends of the clamping member 30 are pressed more strongly against the periphery of the catheter 11, while the region intermediate the ends is pressed less strongly to the catheter or is even lifted therefrom. By this means, two pressure and sealing regions are created at the ends of the clamping member 30 thus fixing the catheter 11 relative to capsula 10. Further, the catheter passageway is sealed by the connecting piece 22 so that no fluid may flow out of the cavity and externally along the catheter.

As obvious from FIG. 2, only part of the pressure piece 26 projects in radial direction beyond the contour of the capsula 10.

To fix catheter 11 to capsula 10, the pressure member 26 is unscrewed thus relieving the clamping member 30, the catheter 11 being slipped through the pressure member 31 onto the support section 24b of the support canula 24, until the catheter end abuts against the end face 29. Subsequently, the pressure member 26 is tightened, whereby the clamping member 30 assumes the shape shown in FIG. 1 while the catheter is pressed radially against the support region 24b.

FIG. 3 shows an embodiment without a support canula. In this case, the clamping member 30 is supported by the funnel-shaped end face 29 of the housing portion 17. As for the rest, the embodiment of FIG. 3 corresponds to that of FIGS. 1 and 2.

What is claimed is:

1. Implantable catheter means comprising
   a capsula (10) having a cavity (12), a bottom wall (13), a peripheral wall (14) and a top wall (15) pierceable by a needle,
   a connecting piece (22) laterally projecting from the peripheral wall (14) of the capsula (10),
   a catheter (11) insertable into the connecting piece (22),
   an elastomeric clamping member (30) coacting with the connecting piece (22) in order to fix and seal the catheter (11) relative to the connecting piece (22),
   a pressure member (26) adapted to be joined to the connecting piece (22) and encompassing the catheter (11) to press it axially against the clamping member (30) which will be radially deformed accordingly thus sealing the passage of the catheter through the connecting piece (22),
   the connecting piece (22) containing an internal thread (23) into which an external thread of the pressure member (26) may be screwed,
   a rigid tubular support canula (24) which supports from the inside at least the section of the catheter (11) surrounded by the clamping member (30), and
   the support canula (24) being secured to the connection unit with a fixation section (24a) and wherein it unsupportedly projects outwardly relative to the connection piece (22) towards the free end of and coaxially to the latter.

2. Catheter means according to claim 1, characterized in that in the plane of its bottom wall (13), the capsula (10) comprises a peripheral flange (19), and that the connecting piece (22) is provided avove the flange (19) without projecting from it laterally.

3. Catheter means according to claim 2, characterized in that the connecting piece (22) is integrally formed in one part with the flange (19).

4. Catheter means according to claim 1, characterized in that a clamping space to receive the clamping member (30) is provided in the interior of the connecting piece, said clamping space having a funnel-shaped end wall at the end confronted with the cavity (12).

5. Catheter means according to claim 4, characterized in that the clamping space is limited by the pressure member (26) and that the end wall (28) of the pressure member (26) confronted with the clamping member (30) contains a funnel-shaped recess.

6. Catheter means according to claim 1, characterized in that the capsula (10) comprises a first housing portion (16) which forms the bottom wall (13) and a lower part of the peripheral wall (14), and a second housing portion (17) which encompasses laterally the first housing portion (16) and has a collar (18) projecting beyond the top wall (15) and pressing from above against a border of the pierceable top wall (15).

7. Catheter means according to one of claims 2 and 6, characterized in that the connecting piece (22) and the flange (19) are components of the second housing portion (17).

8. Catheter means according to claim 1, characterized in that the support canula (24) comprises a support flange for supporting the clamping member (30).

9. Catheter means according to claim 8, characterized in that the support flange comprises a funnel-shaped end face (29) confronted with the clamping member (30).

* * * * *